(12) United States Patent
Dai et al.

(10) Patent No.: US 8,049,026 B2
(45) Date of Patent: *Nov. 1, 2011

(54) SYNTHESIS OF IONIC LIQUIDS

(75) Inventors: Sheng Dai, Knoxville, TN (US);
Huimin Luo, Knoxville, TN (US)

(73) Assignee: UT-Battelle, LLC, Oakridge, TN (US)

( * ) Notice: Subject to any disclaimer, the term of this patent is extended or adjusted under 35 U.S.C. 154(b) by 220 days.

This patent is subject to a terminal disclaimer.

(21) Appl. No.: 11/971,949

(22) Filed: Jan. 10, 2008

(65) Prior Publication Data

US 2008/0146849 A1    Jun. 19, 2008

Related U.S. Application Data

(63) Continuation of application No. 10/749,450, filed on Dec. 31, 2003, now Pat. No. 7,423,164.

(51) Int. Cl.
*C07F 15/02* (2006.01)
*C07F 15/04* (2006.01)
*C07F 15/06* (2006.01)
*C07F 1/08* (2006.01)
*C07F 1/10* (2006.01)

(52) U.S. Cl. ......... 556/14; 556/111; 549/208; 549/353; 564/82; 564/463

(58) Field of Classification Search ............ 556/14, 556/111; 549/208, 353; 564/82, 463
See application file for complete search history.

(56) References Cited

U.S. PATENT DOCUMENTS

| | | | | |
|---|---|---|---|---|
| 4,218,377 A * | 8/1980 | Stockinger et al. | ........... | 548/403 |
| 4,764,440 A | 8/1988 | Jones et al. | | |
| 5,256,821 A * | 10/1993 | Armand | ............... | 564/82 |
| 5,723,664 A * | 3/1998 | Sakaguchi et al. | ............. | 564/82 |
| 5,731,101 A | 3/1998 | Sherif et al. | | |
| 6,365,301 B1 | 4/2002 | Michot et al. | | |
| 6,379,634 B1 | 4/2002 | Fields et al. | | |
| 6,531,270 B1 | 3/2003 | Olson et al. | | |
| 6,548,567 B2 | 4/2003 | Armand et al. | | |
| 6,573,405 B1 | 6/2003 | Abbott et al. | | |
| 6,620,546 B1 | 9/2003 | Michot et al. | | |
| 6,623,657 B1 | 9/2003 | Berglund et al. | | |
| 7,423,164 B2 * | 9/2008 | Dai et al. | ........... | 556/14 |
| 2002/0001674 A1 | 1/2002 | Uhlenbrock | | |
| 2002/0015883 A1 | 2/2002 | Hilarius et al. | | |
| 2002/0015884 A1 | 2/2002 | Schmidt et al. | | |
| 2002/0161261 A1 | 10/2002 | Bahrmann et al. | | |
| 2003/0080312 A1 | 5/2003 | Seddon et al. | | |
| 2003/0125599 A1 | 7/2003 | Boudreau et al. | | |
| 2003/0149264 A1 | 8/2003 | Wasserscheid et al. | | |
| 2003/0157351 A1 | 8/2003 | Swatloski et al. | | |

FOREIGN PATENT DOCUMENTS

| | | |
|---|---|---|
| WO | WO 03/051874 | 6/2003 |
| WO | WO 03/087390 | 10/2003 |
| WO | WO 03/089389 | 10/2003 |
| WO | WO 03/093246 | 11/2003 |

OTHER PUBLICATIONS

Dillon R.E.A. et al., "Influence of the Anion on the Formation of Amorphous Tonically Conducting Lithium Salt Complexes with 18-C-6 and 2.2.2-Cryptand Macrocycles", *Chem. Mater.* 13(8):2516-2522 (2001).

Davidson M.G. et al., "Structural Diversity in Lewis-Base Complexes of Lithium Triflamide", *Eur. J.Inorg. Chem.* 18:3445-3452 (2003).

Eyring E.M. et al., "Lithium Ion-Crown Ether Complexes in a Molten Salt", *Pure & Appl. Chem.* 65(3):451-454 (1993).

Canadian Office Action dated Oct. 28, 2009.
European Office Action dated Jan. 25, 2010.

* cited by examiner

*Primary Examiner* — Peter O Sullivan
(74) *Attorney, Agent, or Firm* — Scully, Scott, Murphy & Presser, P.C.

(57) ABSTRACT

Ionic compounds which are liquids at room temperature are formed by the method of mixing a neutral organic ligand with the salt of a metal cation and its conjugate anion. The liquids are hydrophobic, conductive and stable and have uses as solvents and in electrochemical devices.

21 Claims, 13 Drawing Sheets

SYNTHESIS OF IONIC LIQUIDS

This application is a continuation of U.S. application Ser. No. 10/749,450 filed on Dec. 31, 2003, now U.S. Pat. No. 7,423,164. The specification of U.S. application Ser. No. 10/749,450 is now incorporated by reference in its entirety.

STATEMENT REGARDING FEDERALLY SPONSORED RESEARCH

This invention was made with United States Government support under Contract No. DE-AC05-96OR 22725 between the United States Department of Energy and Oak Ridge National Laboratory, managed by UT-Battelle, LLC, and the United States Government has certain rights in this invention.

This invention relates to new synthetic routes to the preparation of hydrophobic ionic liquids and the ionic compounds made thereby.

BACKGROUND AND PRIOR ART

Ionic liquids are organic salts with melting points below 100° C. and typically are liquids at room temperature. Early interest in the compounds was based upon their conductivity, as described in U.S. Pat. No. 4,764,440. Ionic liquids may be used as a solvent in a chemical vapor deposition system (U.S. Published Patent Application No. 2002/0001674), as coupler solvents in photothermographic systems (U.S. Pat. No. 6,531, 270), as solvents for Friedel-Crafts and Diels-Alder reactions (U.S. Pat. No. 6,573,405), as a catalyst for isomerisation reactions, (U.S. Published Patent Application No. 2003/0109767), as complexing agents in separations (U.S. Published Patent Application No. 2003/0125599 and U.S. Pat. No. 6,623,659) as a solvent to form regenerated cellulose (U.S. Published Patent Application No. 2003/0157351), and as a polymerization catalyst (WO 03/087390), to name a few.

Ionic liquids may be made by the reaction of an onium chloride with a Lewis acid such as $AlCl_3$. Heterocyclic halides react with lithium borates in acetonitrile to form ionic liquids useful in electrochemical cells (U.S. Published Patent Application No. 2002/0015883) and with lithium trifluorophosphates to form inert solvents (U.S. Published Patent Application No. 2002/0015884). EMICl (1-methyl-3-ethyl imidazolium chloride) may be reacted with potassium bisfluorosulfonimide (KFSI) to yield a conductive liquid useful as a current collector (U.S. Pat. No. 6,365,301). Sulfonated or carboxylated triesters of phosphorous acid may serve as anions for ammonium cations (U.S. Published Patent Application 2002/0161261). Salts of diazonium, sulfonium, iodonium or metallocennium types may be useful in chiral syntheses (U.S. Pat. No. 6,548,567).

An aqueous nitrate of Ag(I) may be reacted with an imidazolium chloride to form an ionic liquid and a silver chloride salt (U.S. Pat. No. 6,379,634). A halide-free ionic liquid may be obtained by reacting a halide salt of an organic cation with a Brønsted acid in an alcohol or hydrocarbon solvent (WO 03/051874).

A two-step continuous process is disclosed in WO 03/089389. WO 03/093246 describes liquids wherein the cation is a nitrogen or phosphorous compound and the anion is a five-member nitrogen heterocycle. A process to minimize halides in ionic liquids is based on fluorinated esters or alkyl sulfonates as replacements for haloalkanes when forming an imidazolium salt (U.S. Published Patent Application No. 2003/0080312) and lower melting temperatures have been obtained when the cation is Zn, Sn or Fe (III) and the anion is a quaternary amine (U.S. Pat. No. 6,573,405).

Chiral ionic liquids may be made from optically active ammonium cations and used for asymmetric syntheses (U.S. Published Patent Application No. 2003/0149264). Metallic cations and perhalogenated substituents on the anionic portion are disclosed in U.S. Pat. No. 6,620,546.

In consideration of the many uses for ionic liquids, a need exists for liquids with different properties with new uses and for new ways to make them.

BRIEF SUMMARY OF THE INVENTION

The invention relates to new methods for the synthesis of ionic compounds, especially liquids, and to the new liquids made by the methods. These liquids are salts that are liquid at room temperature, hence RTIL. The liquids are hydrophobic and compatible with extraction processes and reaction schemes in organic chemistry.

The objectives of this invention may be met using the complexation of cations by neutral ligands. This produces room temperature ionic liquids having cationic coordination metal complexes.

DETAILED DESCRIPTION OF THE INVENTION

Crown ethers are readily available commercially and used primarily in chemical research because the exposed oxygen atoms readily complex with metal ions. Depending on substituents, the crown ethers may have adjustable solubility in aqueous solvents.

When reacted with an alkaline organic salt, crown ethers form coordination metal complexes of the ether and the alkaline metal, together with an organic anion gegenion. The organic salt of many of these compounds is a room temperature ionic liquid with a low volatility and is strongly hydrophobic.

Figure 1A:
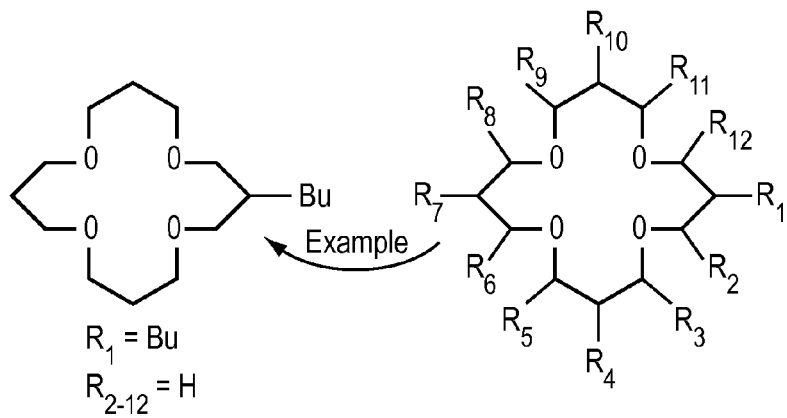
FIGS. 1A and 1B. Examples of suitable crown ethers
Figure 1B:
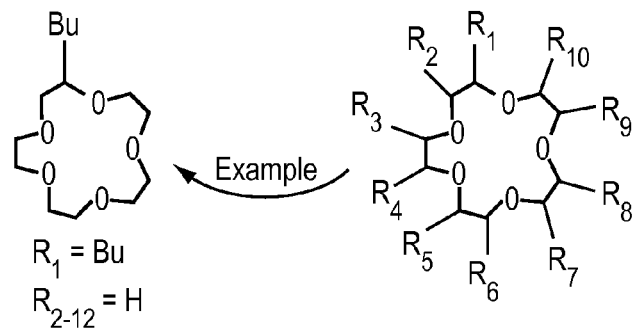

Suitable crown ethers for this purpose are shown in FIG. 1. Reference is made also to catalogues from Aldrich, Gelest and Tokyo Kasei, Kogyo.

Suitable metals are sodium, potassium, lithium and calcium

These reactions are exothermic and require no solvent, heat or catalyst. Excess reagent salt can be washed away.

A similar system may be formed using small cations with neutral organic ligands in what formally appear to be a methathesis reactions, an exchange of anions. Organic amines are representative of the neutral ligand. Silver is a representative small cation and forms stable complexes with amines. Salts such a lithium bis(trifluoromethane)sulfonimide [$(CF_3SO_2)_2$N—Li, "lithiotrifluorosulfonylamide, Li(Tf)$_2$N], $BF_4^-$, $NO_3^-$, $SO_4^-$, $PO_4^{+3}$, $PF_6^-$ and dicyanamide [$N(CN)_2^-$] are suitable for exchange because they supply a suitable bulky anion. Such systems are readily worked-up using water to remove salt residues.

Table 1 shows representative examples of alkyl amine salts, yields and properties.

Suitable metal ions include $Ag^{+1}$, $Zn^{2+}$, $Cu^{2+}$, $Cd^{2+}$, $Ni^{2+}$, $Hg^{2+}$, $Co^{3+}$ ions and $Fe^{3+}$.

Figure 2A:
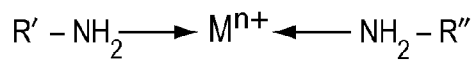
FIGS. 2A, 2B, and 2C. Show structural features of the cations of ionic liquids.
Figure 2B:
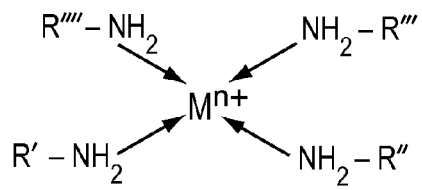
Figure 2C:
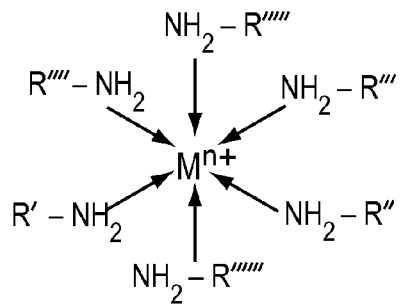

The structural features of the cations of these ionic liquids are given in FIG. 2.

Other neutral ligands for purposes of this invention include sulfur and phosphorous compounds containing neutral ligands.

Experiment 1

Neat cyclohexyl-15-crown-5 (Parish, Inc.), was mixed with an equimolar amount of N-lithiobis(trifluoromethane) sulfonimide Li(Tf)$_2$N in a boiling flask at room temperature without an inert blanket and stirred using a magnetic stir bar. Warming was apparent tactilly and a clear colorless solution obtained.

The same compounds under the same conditions were reacted at a ratio of cyclohexyl-15-crown-5 to Li(Tf)$_2$N of 1:1.35.

No loss of mass was observed during vacuum rotary evaporation at 100° C. for four hours.

Both products were soluble in organic solvents including acetone and acetonitrile but immiscible in water and aqueous solutions.

Figure 3:
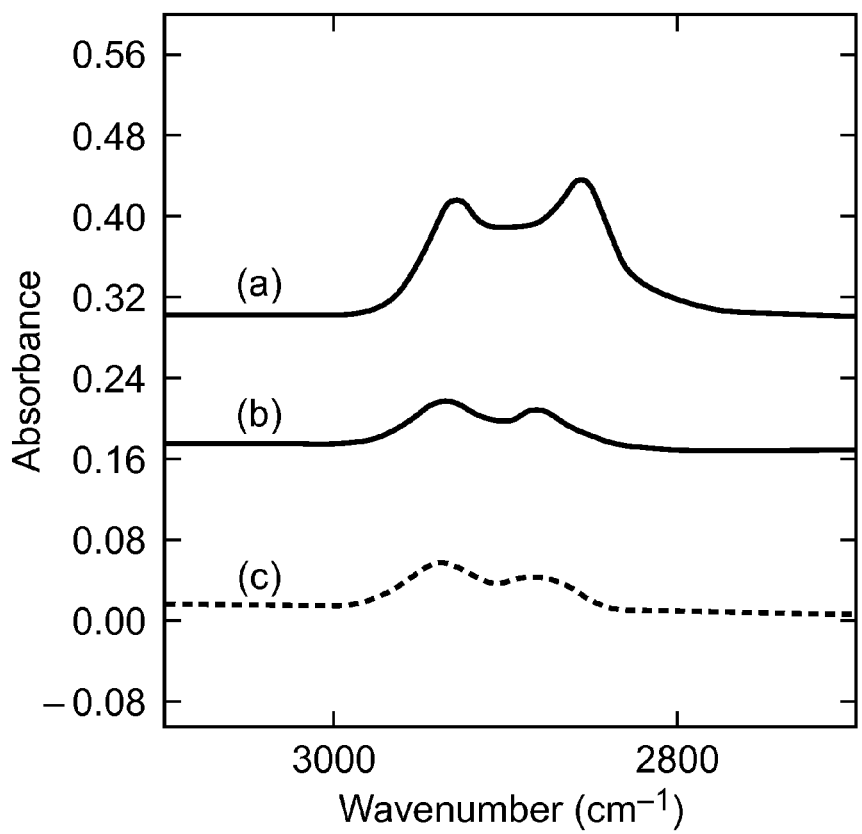
FIG. 3. Shows comparative FTIR spectra of neat cyclohexyl-15-crown-5 (a) of the room temperature ionic liquid obtained by the reaction of the crown ether with $Li(Tf)_2N$ 1:1 (b) and by 1:1.35 reaction of the ether with $Li(Tf)_2N$ (c).

FIG. 3 shows comparative FTIR spectra of neat cyclohexyl-15-crown-5 (a) of the room temperature ionic liquid obtained by the reaction of the crown ether with Li(Tf)$_2$N 1:1 (b) and by 1:1.35 reaction of the ether with Li(Tf)$_2$N. The peak in the region of 2900 cm$^{-1}$ of the neat ether, corresponding to a C—H stretch, has been shifted by complexation as shown in the figure. This is evidence of the complexation of the ether with the lithium cation.

Figure 4:
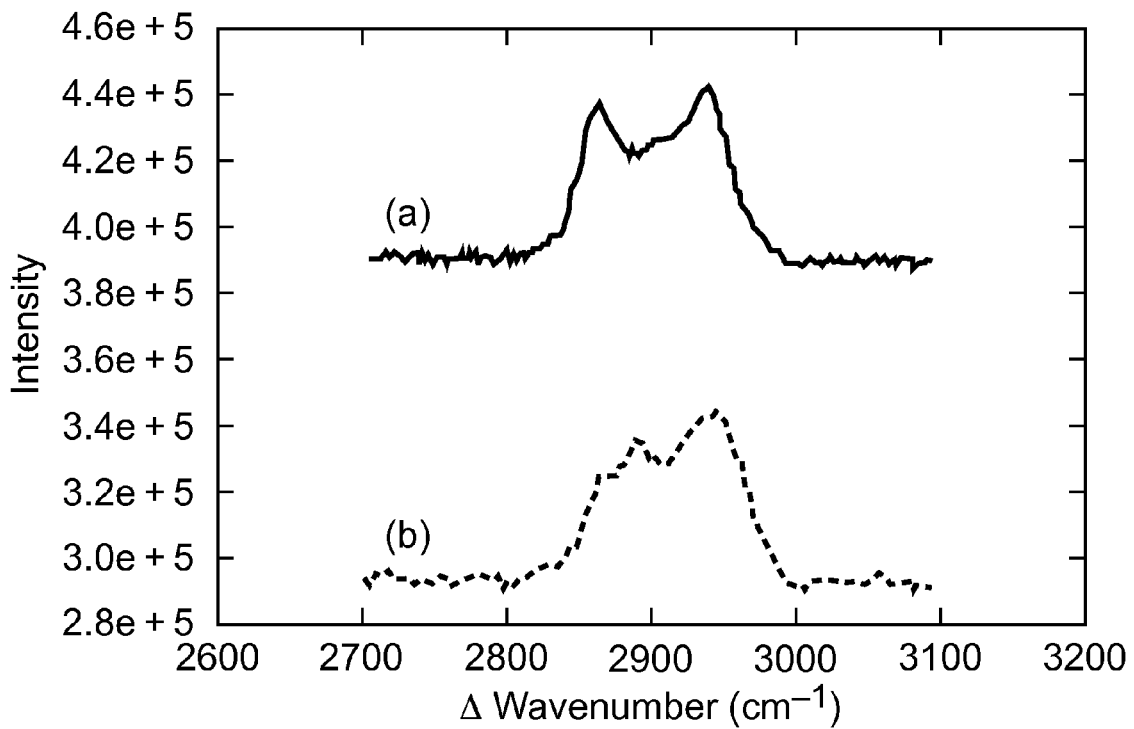
FIG. 4. Shows the comparative Raman spectra in the C—H stretching region of the pure cyclohexyl-15-crown-5 (a) and the RTIL of the 1:1 complex with $Li(Tf)_2N$ (b).

FIG. 4 shows the comparative Raman spectra in the C—H stretching region of the pure cyclohexyl-15-crown-5 (a) and the RTIL of the 1:1 complex with Li(Tf)$_2$N (b).

Example 2

Compounds according to Table 1 were obtained by mixing amines of the formula R$_1$, R$_2$—NH$_2$ with 1:1 aqueous solution of AgNO$_3$ in D.I. water at room temperature with stirring. A stoichiometric amount, based upon amount of R—NH$_2$ of Li(Tf)$_2$N was added to a stirred solution of the Ag (H$_2$NR) (H$_2$NR$_2$) obtained from the first step was added with stirring and the mixture was stirred for one hour and then poured into a separatory funnel. The lower layer of water containing dissolved LiNO$_3$ was drawn off. The RTIL obtained was washed three times with D.I. water and dried using a vacuum rotary evaporator at 80° C. for six hours. The dried product was weighed and the yield calculated based upon Ag.

Table lists the various R-groups used, the yield, density and conductivities measured using a conductivity meter.

Figure 5:
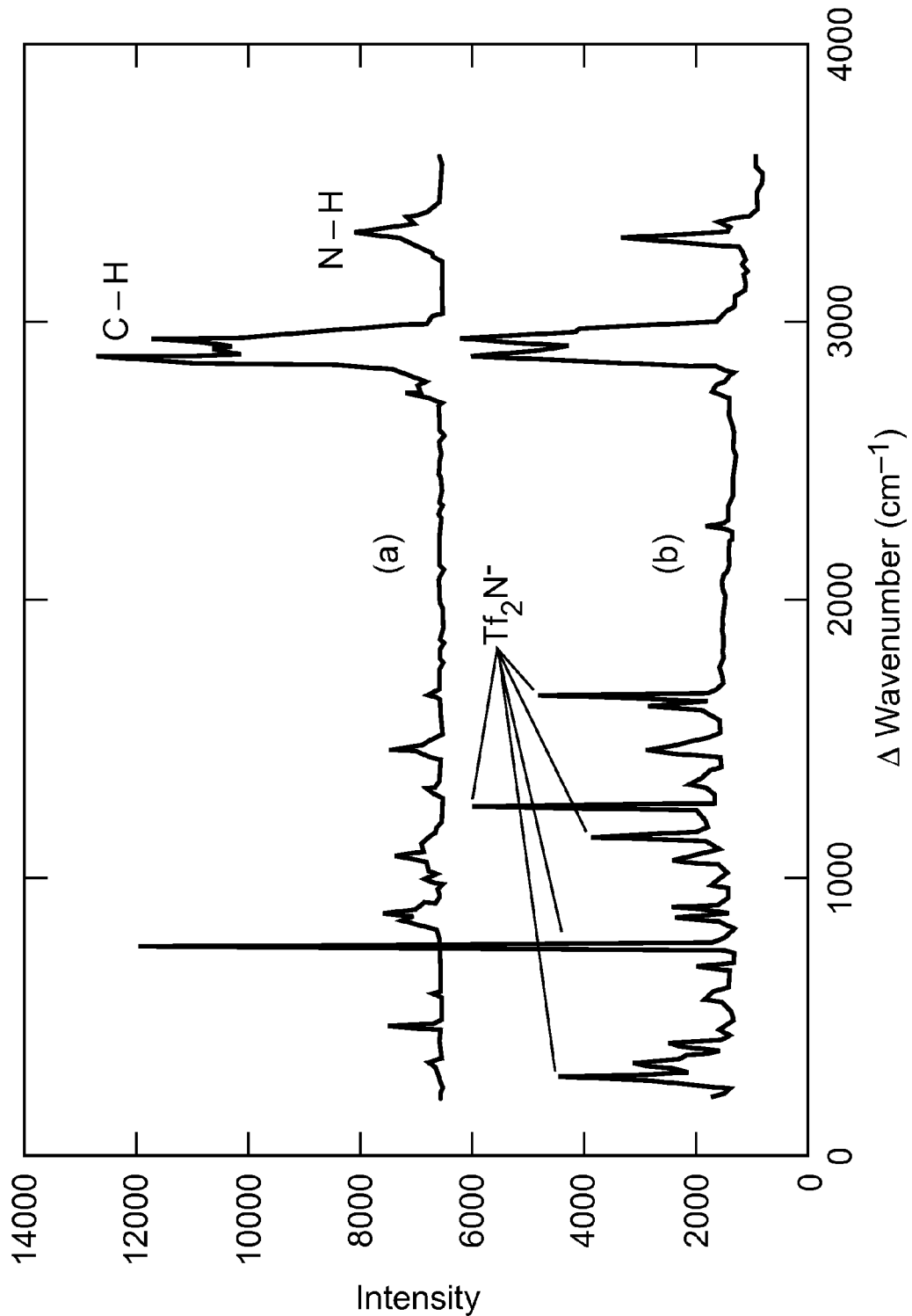
FIG. 5. Shows the Raman spectra of propylamine (a) and $Ag(H_2N—C_3H_7)_2+Tf_2N$ (b).

FIG. 5 shows the Raman spectra of propylamine (a) and Ag(H$_2$N—C$_3$H$_7$)$_2$+Tf$_2$N (b).

Figure 6:
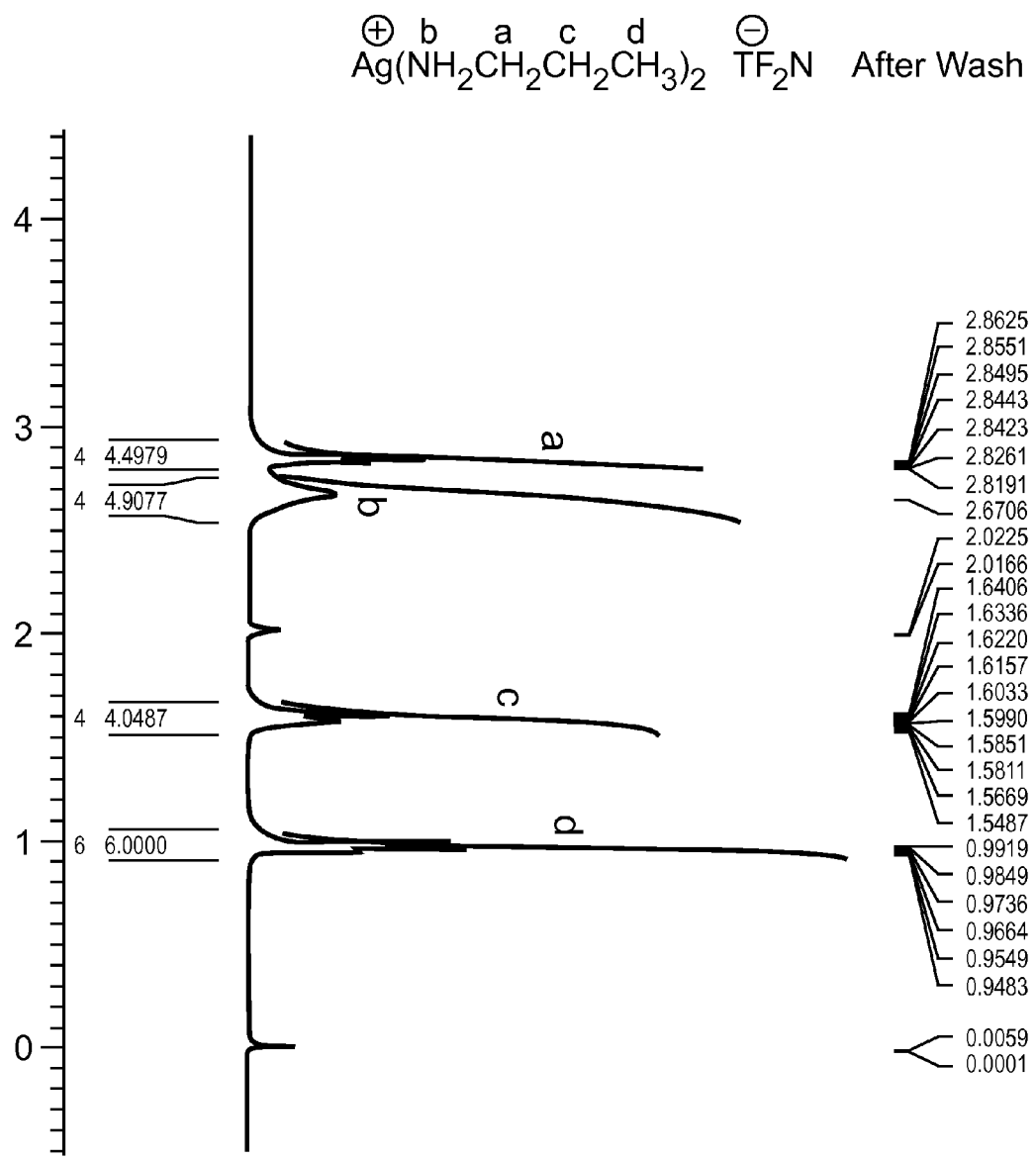
FIG. 6. Shows the proton nmr spectrum of $Ag(H_2N—C_3H_7)_2+(Tf)_2N$ in deuterated chloroform showing the shifts of the amino, ethyl and methyl propyl amine protons and the splitting patterns, together with peak integrations.

FIG. 6 is the proton nmr spectrum of Ag(H$_2$N—C$_3$H$_7$)$_2$+ (Tf)$_2$N in deuterated chloroform showing the shifts of the amino, ethyl and methyl propyl amine protons and the splitting patterns, together with peak integrations.

Figure 7:
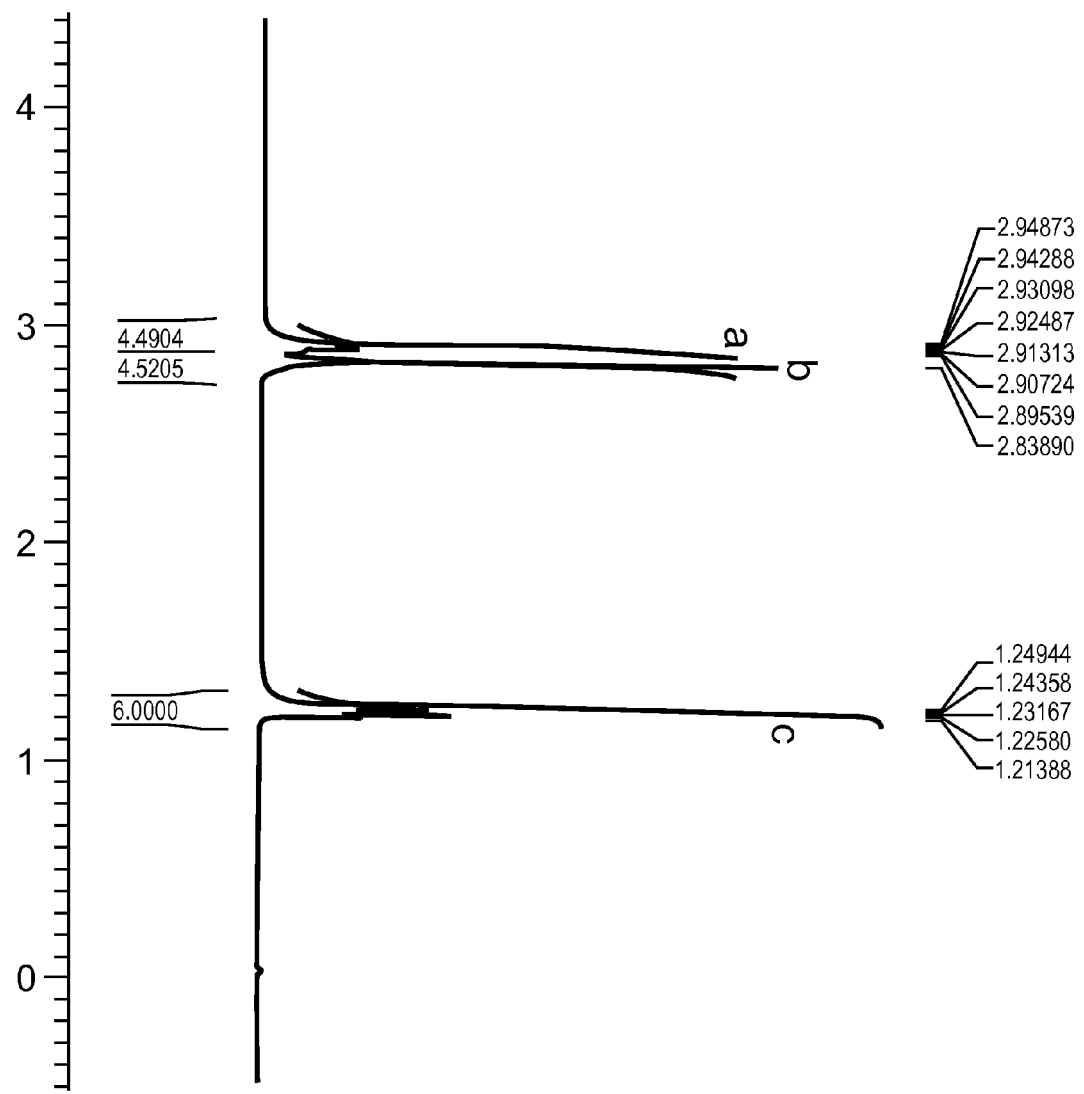
FIG. 7. Shows the nmr spectrum for $Ag(NH_2R_1)(NH_2R_2)$ wherein $R_1=R_2=C_2H_5$.
Figure 8:
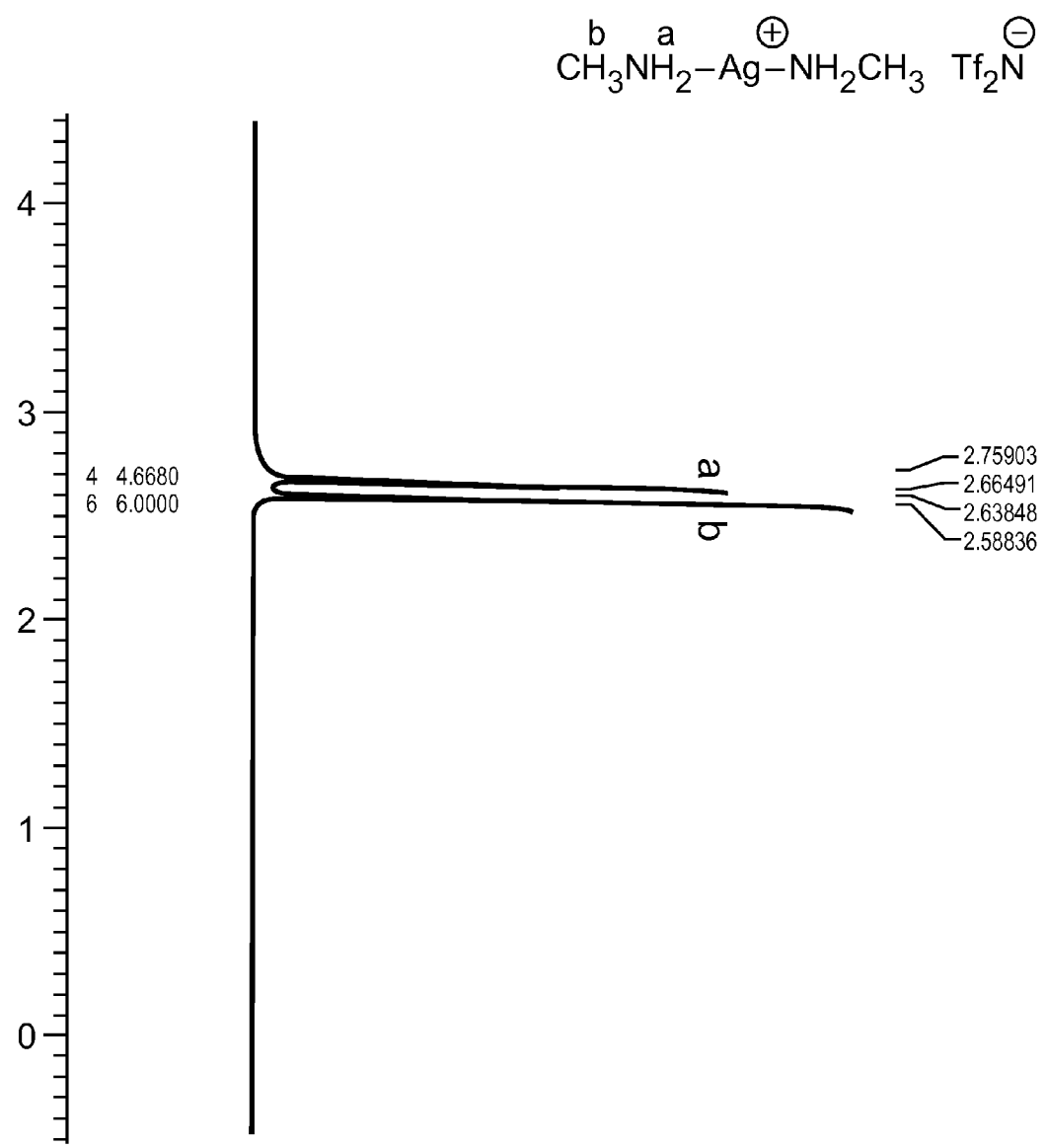
FIG. 8 Shows the nmr spectrum for $R_1=R_2=CH_3$.
Figure 9:
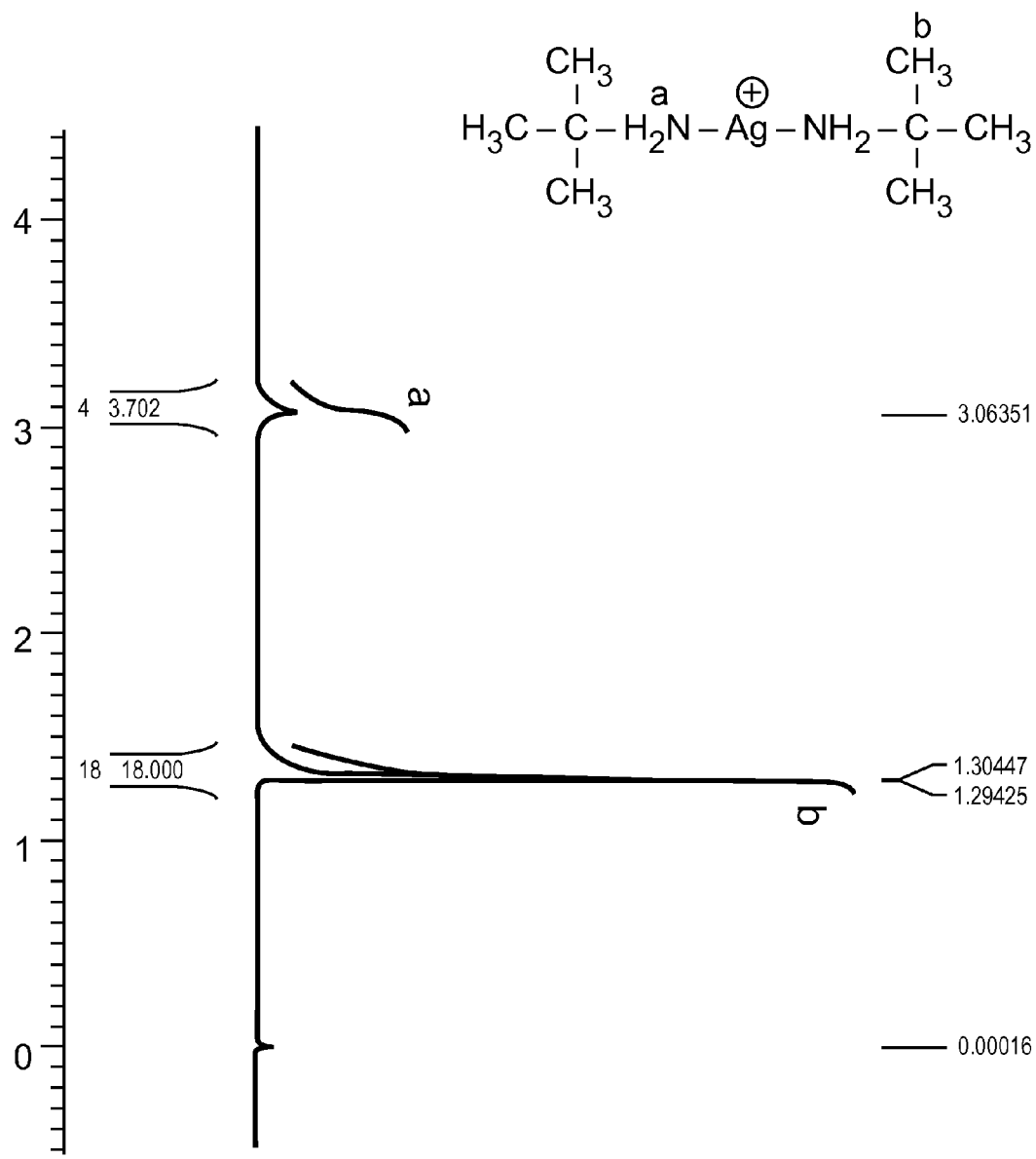
FIG. 9. Shows the nmr spectrum for $R=R_2=tert\text{-butyl}$.
Figure 10:
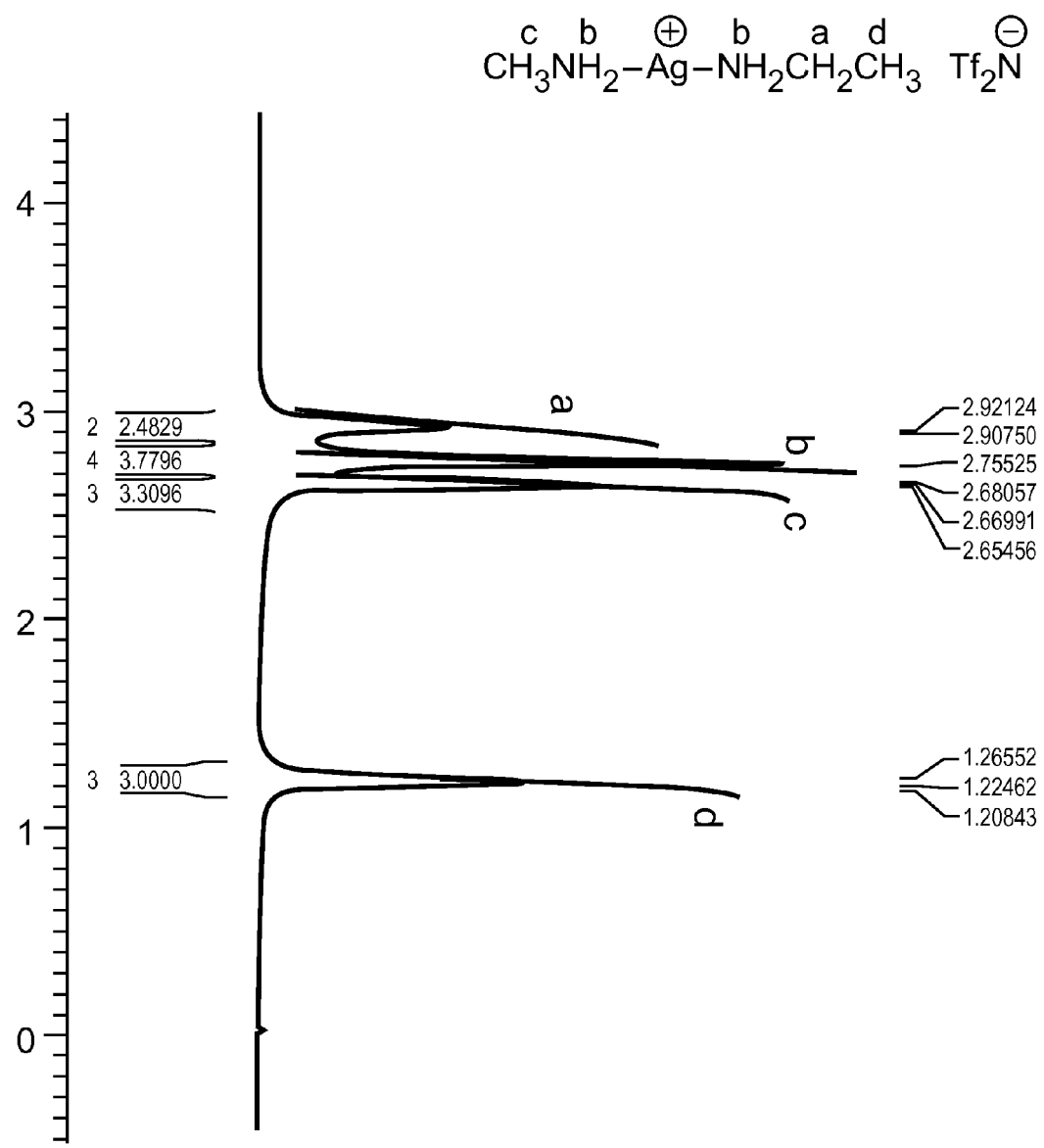
FIG. 10. Shows the proton nmr spectra for mixed amines, for $R_1=CH_3$, $R_2=C_2H_5$.
Figure 11:
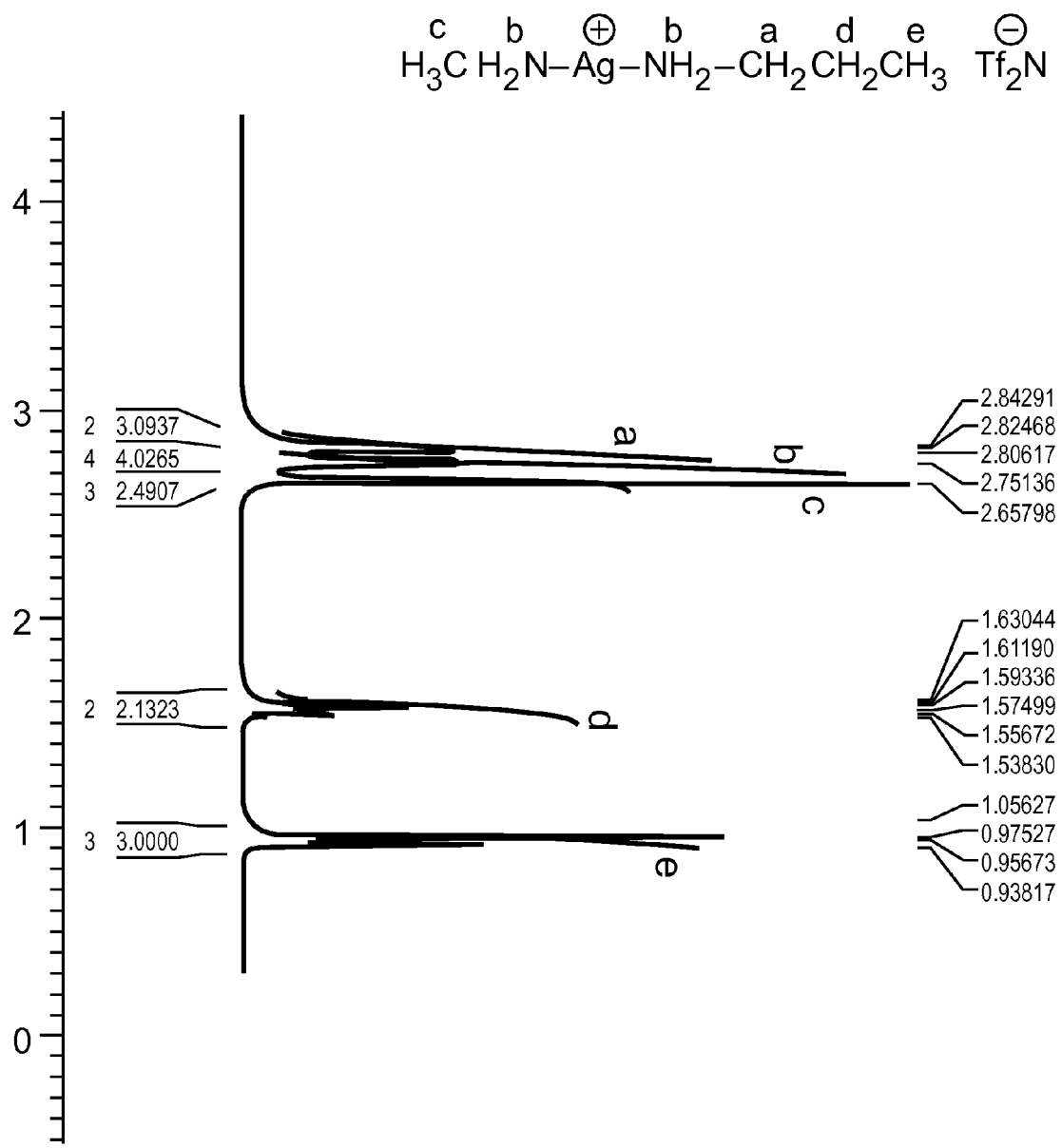
FIG. 11. Shows the proton nmr spectra for mixed amines, for $R_1=CH_3$, $R_2=C_3H_7$.
Figure 12:
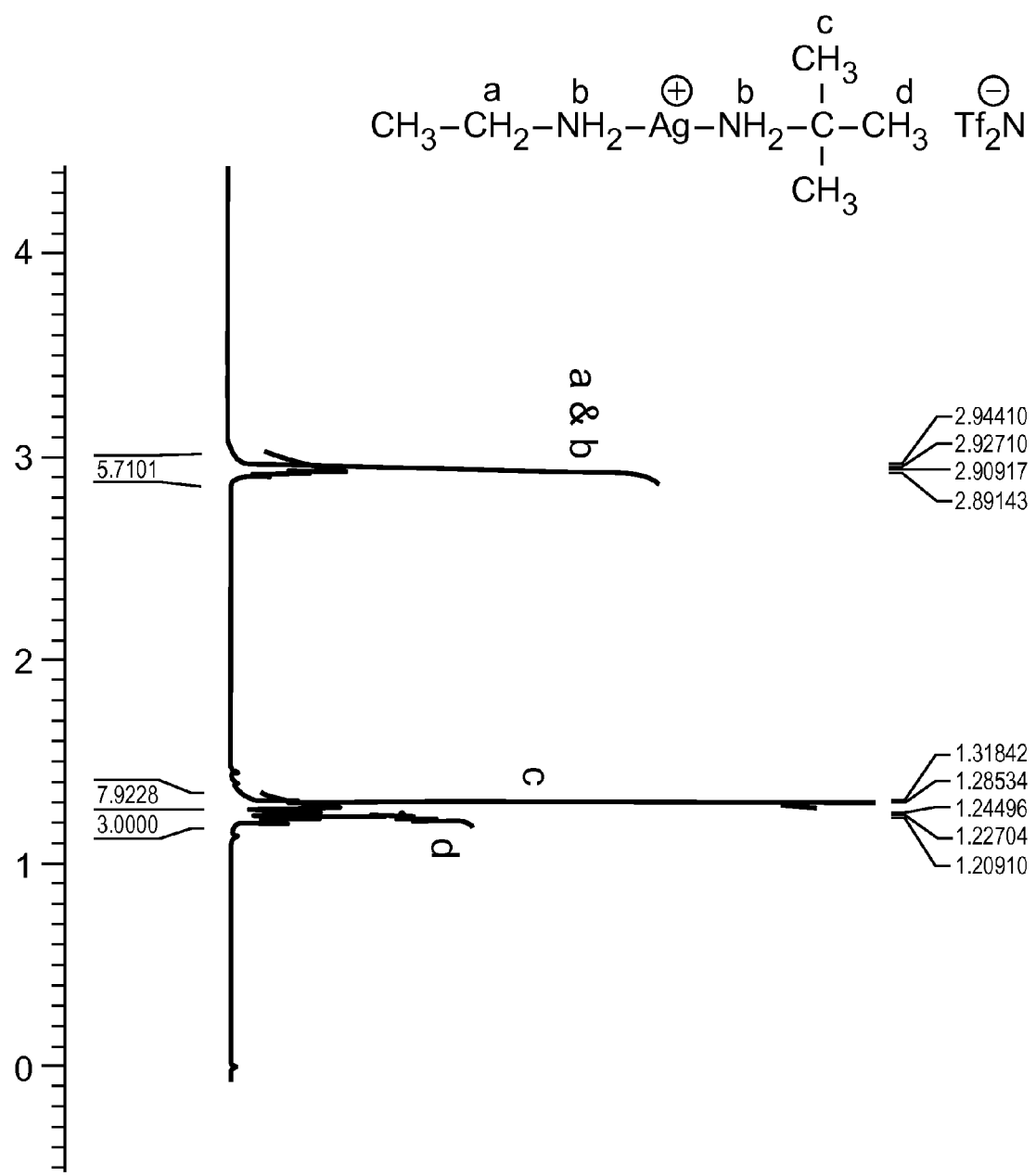
FIG. 12. Shows the proton nmr spectra for mixed amines, for $R_1=CH_3$; $R_2=tert\text{-butyl}$.
Figure 13:
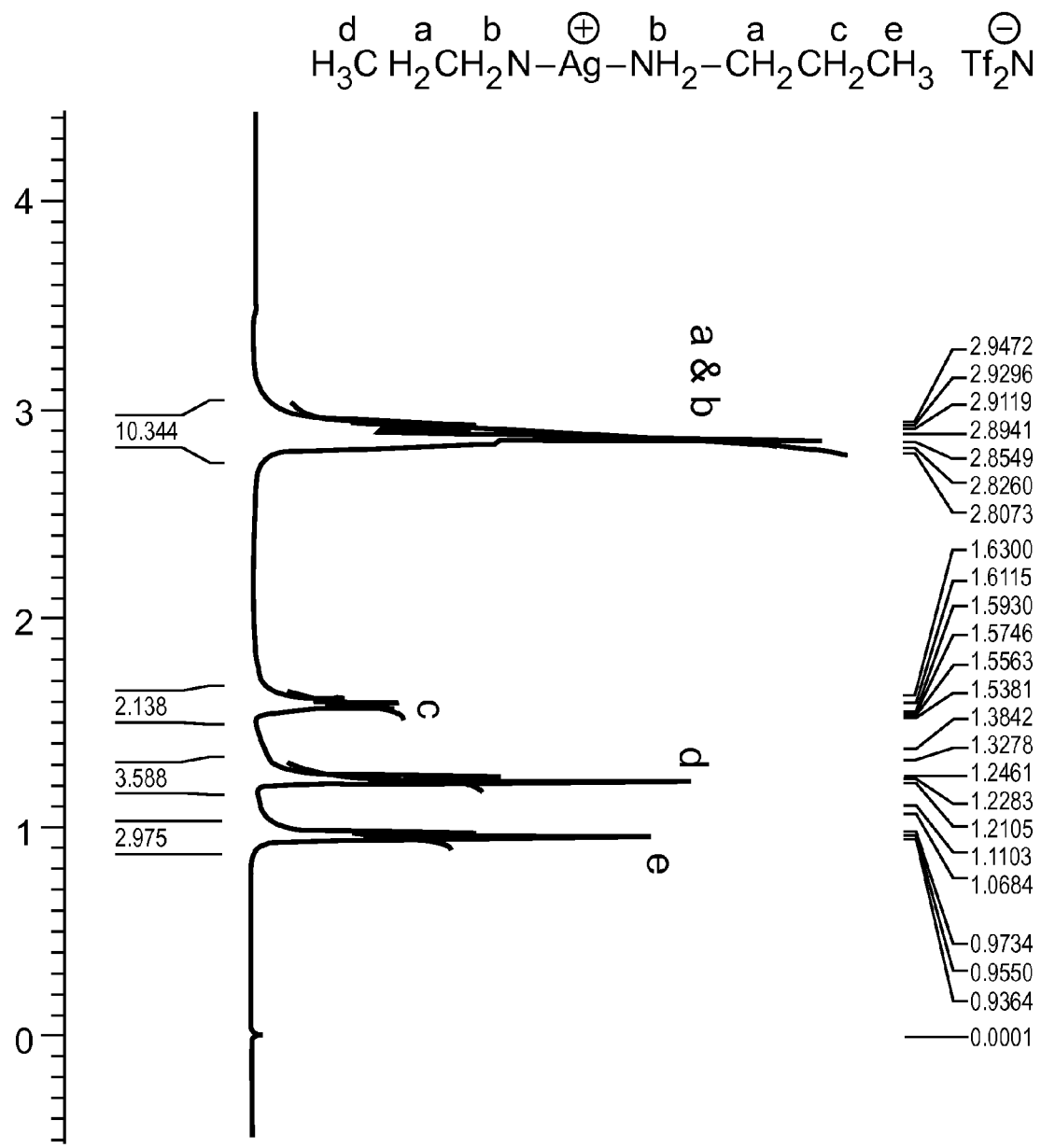
FIG. 13. Shows the proton nmr spectra for mixed amines, for $R_1=CH_3CH_2$, $R_2=C_3H_7$.
Figure 14:
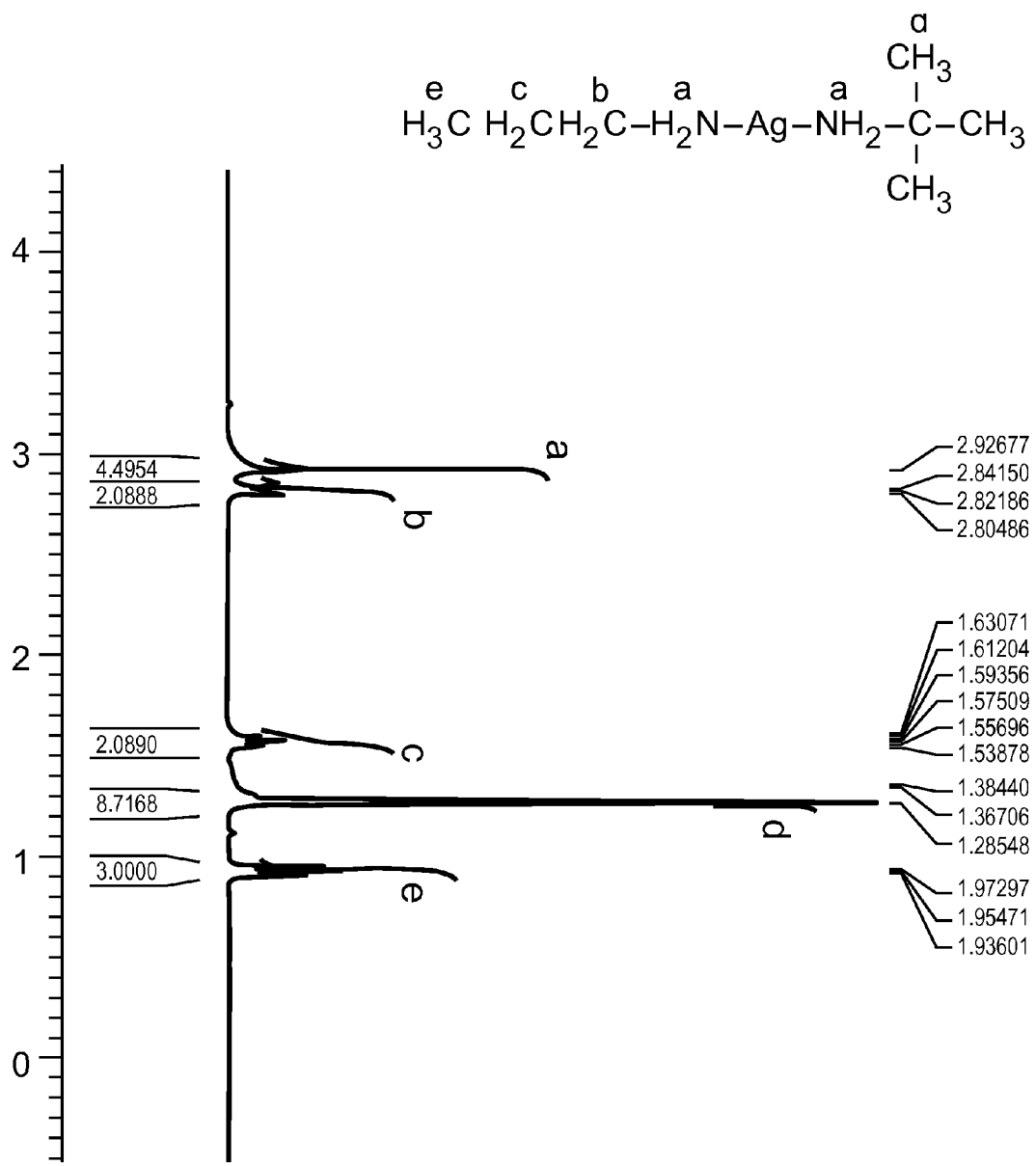
FIG. 14. Shows the proton nmr spectra for mixed amines, for $R_1=CH_3CH_2CH_2$, $R_2=tert\text{-butyl}$.

FIG. 7 is the nmr spectrum for Ag(NH$_2$R$_1$)(NH$_2$R$_2$) wherein R$_1$=R$_2$=C$_2$H$_5$;

FIG. 8 is the nmr spectrum for R$_1$=R$_2$=CH$_3$;

FIG. 9 is nmr spectrum for R=R$_2$=tert-butyl;

FIGS. 10 through 15 are the proton nmr spectra for mixed amines;

FIG. 10 is for R$_1$=CH$_3$, R$_2$=C$_2$H$_5$;

FIG. 11 is for R$_1$=CH$_3$, R$_2$=CH$_3$H$_7$;

FIG. 12 is for R$_1$=CH$_3$, R$_2$=tert-butyl;

FIG. 13 is for R$_1$=CH$_3$CH$_2$, R$_2$=C$_3$H$_7$;

FIG. 14 is for R$_1$=CH$_3$CH$_2$CH$_2$, R$_2$=tert-butyl;

It is noted that in all cases the shifts, splits and integrations shown in the figures are consistent and predictable for the structures.

Figure 15:
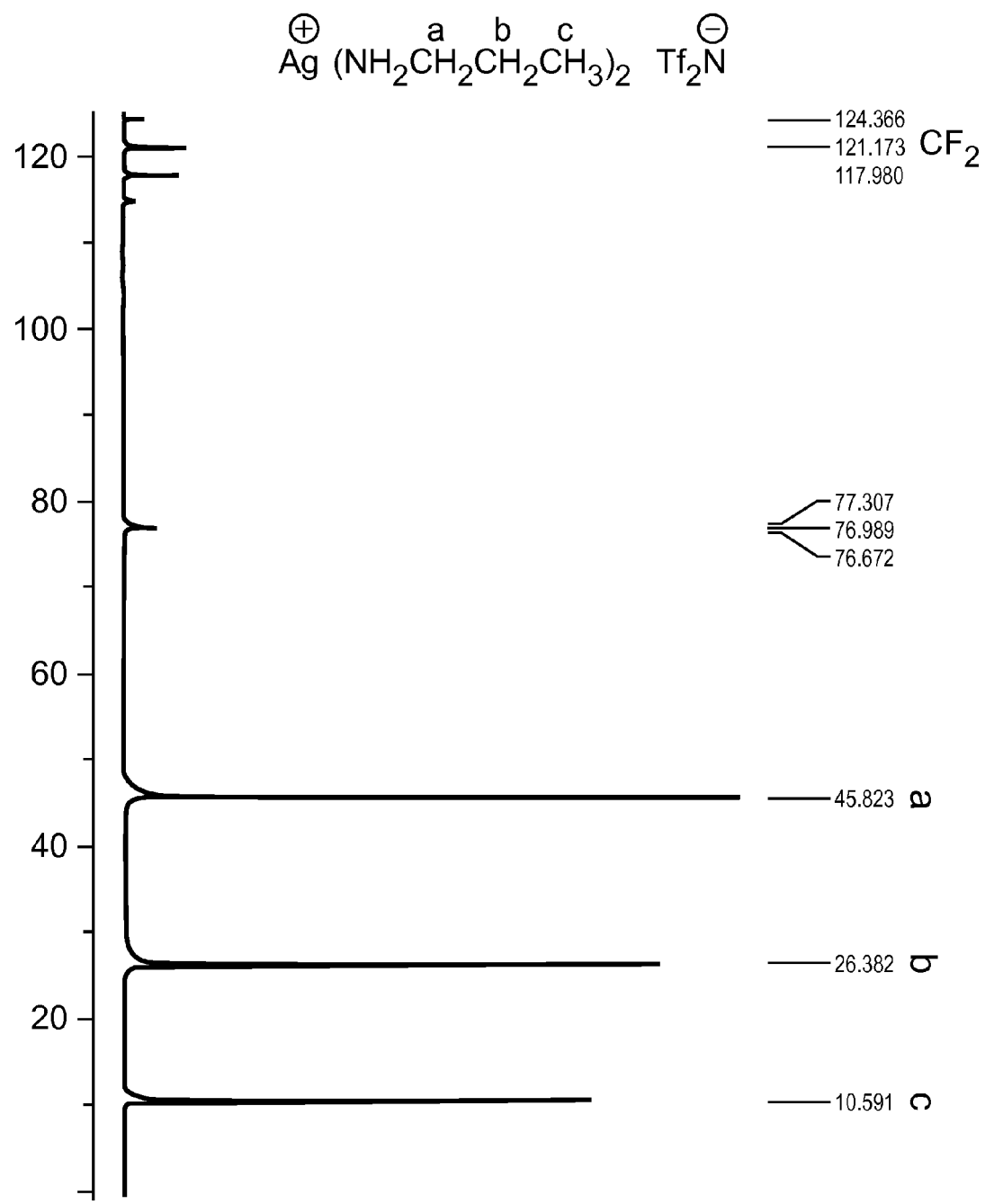
FIG. 15. Shows the carbon −13 nmr of $R_1=R_2=CH_3CH_2CH_2$ in deuterated chloroform.

FIG. 15 is the carbon –13 nmr of R$_1$=R$_2$=CH$_3$CH$_2$CH$_2$ in deuterated chloroform. Whereas the proton shifts were determined at 400.13 MHz, these data were obtained at 100.61 MHz. The internal standard for both sets of spectra was tetramethylsilane (TMS). The expected fluoride shifts for the trifluoromethyl group is quite discernable.

The RTIL of this invention are unique because they are the first such liquids having an inorganic cation complexed with a neutral organic ligand. They have conductivities comparable to the traditional EMI+ salts but are formed by different processes allowing a greater tuning by changing substituents on the organic ligand. These compounds are believed to be useful co-solvents in the separation of metal salts from contaminated aqueous systems, especially systems contaminated with soluble radioactive compounds such as those with strontium, cesium, silver, copper and lanthanum salts. They are also useful in the separation of alkanes from olefins, with particular application to propane:propylene system. This may be useful as liquid separation membrane for gasses, as sensing transducers, electrolyte for super capacitors, as stationary phases for chromatography and as heat transfer fluids. This invention has been described in terms of representative examples. Modifications and additions obvious to those with skills in the art are subsumed within the scope of the invention.

TABLE 1

Densities, conductivities, and synthesis yields for (R$_1$—NH$_2$—Ag$^+$—H$_2$H—R$_2$)Tf$_2$N$^-$ ionic liquids.

| R$_1$ | R$_2$ | Synthesis Yield | Density at 24° C. | Conductivity mS/cm at 24° C. |
|---|---|---|---|---|
| Methyl | Methyl | 68.2 | 1.86 | 12.30 |
| Ethyl | Ethyl | 78.2 | 1.73 | 8.07 |
| Propyl | Propyl | 93.0 | 1.63 | 3.98 |
| t-Butyl | t-Butyl | 76.6 | N/A$^a$ | N/A$^a$ |
| Methyl | Ethyl | 76.3 | 1.80 | 9.70 |
| Methyl | Propyl | 82.6 | 1.74 | 6.42 |

TABLE 1-continued

Densities, conductivities, and synthesis yields for
($R_1$—$NH_2$—$Ag^+$—$H_2H$—$R_2$)$Tf_2N^-$ ionic liquids.

| $R_1$ | $R_2$ | Synthesis Yield | Density at 24° C. | Conductivity mS/cm at 24° C. |
|---|---|---|---|---|
| Methyl | t-Butyl | 79.1 | N/A[a] | N/A[a] |
| Ethyl | Propyl | 85.6 | 1.69 | 5.00 |
| Ethyl | t-Butyl | 86.0 | 1.63 | 2.20 |
| Propyl | t-Butyl | 85.5 | 1.55 | 1.70 |

[a]The corresponding salts are solid at room temperature.

We claim:

1. An ionic liquid comprising a cation, which is a complex of a neutral organic ligand and a metal ion, and an anion, wherein said neutral organic ligand is a crown ether.

2. An ionic liquid according to claim 1 which is a liquid below 100° C.

3. An ionic liquid according to claim 2 which is a liquid at room temperature.

4. An ionic liquid according to claim 1 which is electrically conductive in the absence of a solvent.

5. An ionic liquid according to claim 1 wherein said anion is selected from the group consisting of bis(trifluoromethane) sulfonimide, boron trifluoride, nitrate, sulfate, phosphate, hexafluorophosphate and dicyanamide.

6. A method for forming an ionic liquid comprising mixing a neutral organic ligand with the salt of a metal cation and its conjugate anion at room temperature, wherein said neutral organic ligand is a crown ether.

7. A method according to claim 6 wherein the metal cation is selected from the group consisting of sodium, potassium, lithium and calcium.

8. An ionic liquid comprising a cation, which is a complex of a neutral organic ligand and a metal ion, and an anion, wherein said neutral organic ligand is at least one alkylamine.

9. An ionic liquid according to claim 8 which is a liquid below 100° C.

10. An ionic liquid according to claim 9 which is a liquid at room temperature.

11. An ionic liquid according to claim 8 which is electrically conductive in the absence of a solvent.

12. An ionic liquid according to claim 8 wherein said metal cation is selected from the group consisting of silver, zinc, copper, cadmium, nickel, mercury, cobalt, and iron.

13. An ionic liquid according to claim 8 wherein said anion is selected from the group consisting of bis(trifluoromethane) sulfonimide, boron trifluoride, nitrate, sulfate, phosphate, hexafluorophosphate and dicyanamide.

14. An ionic liquid according to claim 8 wherein said at least one alkylamine ligand has a structure according to the following formula:

$H_2NR$ wherein R is an alkyl group containing 1 to 4 carbon atoms.

15. A method for forming an ionic liquid comprising mixing a neutral organic ligand with the salt of a metal cation and its conjugate anion at room temperature, wherein said neutral organic ligand is at least one alkylamine.

16. A method according to claim 15 wherein said metal cation is selected from the group consisting of silver, zinc, copper, cadmium, nickel, mercury, cobalt, and iron.

17. A method according to claim 15 wherein said conjugate anion is selected from the group consisting of bis(trifluoromethane)sulfonamide, boron trifluoride, nitrate, sulfate, phosphate, hexafluorophosphate and dicyanamide.

18. An ionic liquid according to claim 1 wherein said metal cation is selected from the group consisting of sodium, potassium, lithium and calcium.

19. A method according to claim 6 wherein said conjugate anion is selected from the group consisting of bis(trifluoromethane)sulfonamide, boron trifluoride, nitrate, sulfate, phosphate, hexafluorophosphate and dicyanamide.

20. An ionic liquid comprising a cation of the following formula:

$R_1$—$NH_2$—$Ag^+$—$H_2N$—$R_2$ wherein $R_1$ and $R_2$ are independently selected from alkyl groups containing 1 to 4 carbon atoms, and said cation is complexed with and an anion.

21. An ionic liquid according to claim 20 wherein said anion is selected from the group consisting of bis(trifluoromethane)sulfonamide, boron trifluoride, nitrate, sulfate, phosphate, hexafluorophosphate and dicyanamide.

* * * * *